United States Patent [19]

O'Donnell et al.

[11] Patent Number: 4,905,498
[45] Date of Patent: Mar. 6, 1990

[54] GASEOUS DETECTION SYSTEM

[75] Inventors: Jack O'Donnell, Peoria; Larry Allen, North Pekin; Dato V. Olivero, Dunlap; Jean W. Tegg, Morton, all of Ill.

[73] Assignee: Illinois Air-Tech, Ltd., Peoria, Ill.

[21] Appl. No.: 221,471

[22] Filed: Jul. 19, 1988

Related U.S. Application Data

[63] Continuation-in-part of Ser. No. 892,817, Sep. 11, 1986, abandoned.

[51] Int. Cl.⁴ .............................................. G01N 31/08
[52] U.S. Cl. .................................... 73/23.1; 340/632; 340/576; 180/272
[58] Field of Search .................... 73/23.1, 2.7; 422/84, 422/89, 98; 436/161; 340/632, 576; 180/272

[56] References Cited

U.S. PATENT DOCUMENTS

| | | | |
|---|---|---|---|
| 3,566,674 | 3/1971 | Talroze et al. | 73/23.1 |
| 3,690,833 | 9/1972 | Luckey | 422/84 |
| 3,818,434 | 6/1974 | Gotoh et al. | 340/576 |
| 3,824,538 | 7/1974 | Slemp | 340/576 |
| 3,937,061 | 2/1976 | Rhodes, Jr. | 73/23.1 |
| 4,100,790 | 7/1919 | Harvey | 73/23.1 |
| 4,149,402 | 4/1979 | Manes | 73/23.1 |
| 4,404,065 | 9/1983 | Matson | 436/161 |
| 4,809,810 | 3/1989 | Elfman et al. | 422/84 |

FOREIGN PATENT DOCUMENTS 88439  9/1983  Fed. Rep. of Germany ........ 422/89

Primary Examiner—Hezron E. Williams
Attorney, Agent, or Firm—Henderson & Sturm

[57] ABSTRACT

A gaseous detection system for detecting the existence of a certain gas and further the detection of a certain level or percentage of that certain gas within a certain environment. An example is use of the gas detection system in a motor vehicle to aid in determining when a driver of the motor vehicle may be driving under the influence of alcohol, and for providing an appropriate warning signal that may be viewed from the exterior of the motor vehicle. The system includes a sensor unit (214) for sensing ethanol in the atmospheric contents of the motor vehicle's interior, for example, a unit for providing an actuation signal in response to the sensing unit (214), and a signal unit (233) that generates a signal which can be utilized for many purposes, for example, causing at least some of the exterior lights on the motor vehicle to alternately flash on and off in a substantially non-standard pattern. The sensing unit (214) may also be coupled with a digital read-out device or the like to indicate the amount of blood alcohol content of a person for evidentiary or like purposes.

47 Claims, 5 Drawing Sheets

GASEOUS DETECTION SYSTEM

This application is a continuation-in-part of U.S. application Ser. No. 892,817, filed Sept. 11, 1986, now abandoned.

TECHNICAL FIELD

This invention relates generally to a gaseous detection system for detecting the presence of and determining the level of a preselected gas. One particular application of the system relates generally to alcohol detection, and more particularly to the detection of gaseous alcohol components in a motor vehicle interior compartment, the sensing of which can be utilized to prompt an appropriate warning system such that various persons, including members of the law enforcement community, will be alerted that the motor vehicle in question may be being driven by an intoxicated individual.

BACKGROUND ART

It has long been recognized that detection of certain gases is necessary for the safety or well-being of human life. Indeed, coal miners used the canary to warn them of the presence of life endangering gases. The art has progressed until today there are many systems of gas detection, i.e., infrared, gas chromatography, etc. These systems to date, have required costly and elaborate equipment and reference materials to be reliable. One primary use for such a detection system has been its installation in vehicles to attempt to detect the presence of breath alcohol, i.e., ethanol, in the exhalation of the driver.

In the field of chromatography as used for gaseous detection, the conventional arrangement requires a pure gas to be used as the carrier of the sample being tested. This requires a source of pure gas to be readily available wherever and whenever the gas detection equipment is to be used. Infrared detection of gases requires a source of infrared spectrum including a power source which does not lend itself to economical usage of equipment.

There is therefore a need for simple, economical and reliable equipment and a process to detect individual gases accurately, both as to presence and quantity.

It has long been recognized that driving a motor vehicle while under the influence of alcohol constitutes a serious problem for society. This practice has been statistically shown to contribute to a great loss of life, limb and property, and such losses are not limited to only those individuals who incur the risk by driving while intoxicated. Many laws have been passed by various states in an attempt to control this situation. Such laws provide for a variety of penalties, including fines, prison terms and loss of driving privileges, as well as requiring reeducation regarding safe and proper driving practices. Though such laws no doubt aid in preventing some abuses, these actions do not represent a completely adequate solution.

In the early 1970's, the National Highway Traffic Safety Administration sought to encourage development of an alcohol safety interlock system for use with motor vehicles. Simply described, the Administration sought a device that would reliably detect the presence of an intoxicated driver behind the wheel of a vehicle, and prevent the vehicle from being driven. One way of accomplishing the latter was to disable the ignition. Certain disadvantages are associated with such a system. For instance, the vehicle cannot be used in an emergency, may present a danger to other traffic in the vicinity, and there is a problem with general public acceptability. Because of these problems, the alcohol safety interlock system failed to lead to a generally acceptable and useful device.

Efforts were then made to develop a system that would provide warnings that an intoxicated person was driving a particular motor vehicle. One particular system constructed required the driver to pass a brief test using the steering wheel before the vehicle could be driven in a normal manner. That device has failed to adequately detect intoxication and has been abandoned by the government. There still remain a number of problems with any system making the intoxication determination dependent upon an impairment test. Error presents a serious concern.

There therefore still exists a need for a vehicle alcohol detection warning system that will reliably detect the presence of an intoxicated driver, i.e., one with a predetermined breath alcohol level and that will provide not only a recordable evidentiary quality determination of such breath alcohol level, but also a socially acceptable, yet easily noticeable warning to the public and to law enforcement officials that the driver of the vehicle in question probably is intoxicated. Such a system should be easily manufactured, durable of construction and relatively inexpensive. Further, such a system should be relatively simple to install in a motor vehicle. Additionally, such a system must be senstive only to breath alcohol level, i.e., ethanol. The prior art has been unable to distinguish between ethanol and other gases, and therefore has proved ineffective for detection purposes.

DISCLOSURE OF INVENTION

In the present invention, a means for detecting the gas, the level of which is to be determined is provided, which means comprises: sample or suspect air intake means so positioned to likely receive samples of gas to be detected; a second air intake means positioned so as to be likely not to receive samples of gas to be detected, but to receive fresh environment or amblent air; an isolation unit which will provide the preselected gas in substantially isolated form at its output; a sensor unit for detecting the presence of the preselected gas; a comparison unit for determining the level of the preselected gas; and means for generating a signal in response to the detection of said gas.

In this invention, an isolation unit is used to segregate specific gases (if present), such as ethanol gas, from other gases. A number of valves and pneumatic pathways are used to control the functioning of the isolation unit, and the functioning of the sensor unit with respect thereto. The comparison operation carried out in this invention with respect to the sensor unit output also make use of a dynamically established reference value that is renewed each cycle and that is based on the sensor's own operation. This assures continual accuracy even over a time when known gas sensors vary their sensitivites and operating characteristics, or require pure reference gases.

Additional functions may be added as described herein, but to the isolation unit, the comparison operation as related to the sensor unit, the sensor and the actuation signal generated by the presence of the gas or gases detected comprise the detection system.

Further, a cycle completion unit can be provided that assures that the complete sensing cycle, once initiated, is carried to its conclusion. For instance, if actuating the vehicle ignition initiates the process, the cycle completion unit will cause the invention to complete the analysis procedure even if the ignition system is switched off.

Additionally, a timed storage unit serves to store an actuation signal for the signal unit if a triggering amount of ethanol is present in the sample mixture, even if the ignition is switched off for a period of time. This prevents an individual from initiating the process, and then leaving the vehicle switched off for a few minutes in order to attempt to circumvent the invention's signalling features.

This gas detection embodiment is operable to provide a discernible blood alcohol content of a person's breath sample, as by a bar graph or other digital read-out device, for example, for evidentiary or like purposes.

Although the following description of the best mode relates to use of the invention in connection with a motor vehicle, it should be emphasized that the invention can be utilized in the driving, steering or piloting compartment of any type vehicle whether on land, sea or air, wherein the detection of an intoxicated operator or operators is desirable. It can also be utilized as a gas detection system for testing for presence of gases in most environments where such testing is done today.

BRIEF DESCRIPTION OF THE DRAWINGS

These and other attributes of the invention will become more clear upon a thorough review and study of the following description of the best mode for carrying out the invention, wherein.

BEST MODE FOR CARRYING OUT THE INVENTION

Figure 1:
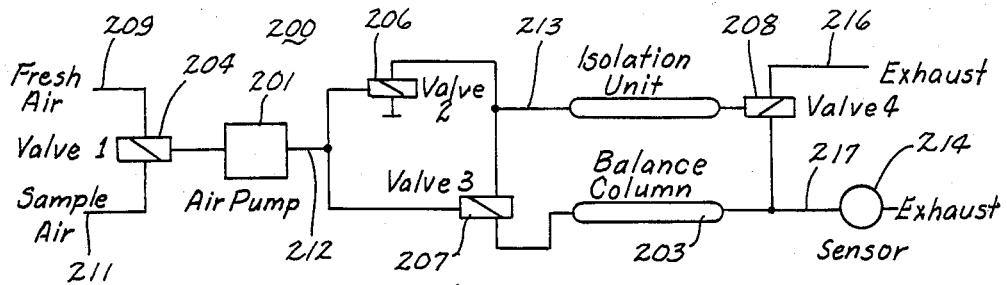
FIG. 1 comprises a schematic diagram of the pneumatic system of this invention.

The invention claimed hereinafter will now be described in the environment of a vehicle to detect breath alcohol, i.e., ethanol, but is not to be so limited. The embodiment hereof includes both pneumatic and electronic elements. The pneumatic elements will be described first as depicted generally in FIG. 1 by the numeral 200.

The pneumatic elements (200) for this embodiment include generally a pump (201), an isolation unit (202), a balance column (203), four valves (204, 206, 207, and 208), and numerous pneumatic pathways that will be described below as appropriate.

Figure 5:
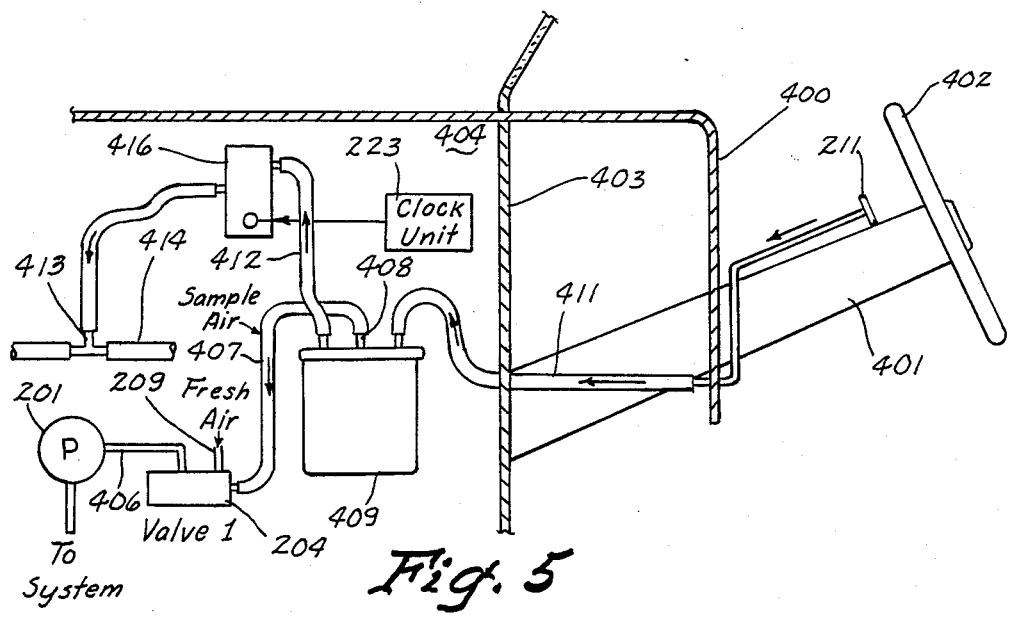
FIG. 5 is a schematic illustrating apparatus within a conventional vehicle for assisting the suction capability of the gas detection system of this invention.

The pump (201) has an intake connected through a pneumatic pathway (205) to the first valve (204). The first valve (204) operates to connect this pneumatic pathway (205) to either a fresh air intake (209) or a sample air intake (211). The fresh air intake (209) should be positioned within the vehicle (not shown) to receive an air sample that will not likely include representative quantities of the breath exhalations of the driver of the vehicle. For example, an interior compartment position located sufficiently distant from the driver, would be suitable. The suspect or sample air intake (211), on the other hand, should be located in a position to likely receive representative breath exhalations of a driver of the vehicle. For instance, the sample air intake (211) could be mounted on the steering wheel column (401) (FIG. 5).

Should it be desirable, however, to obtain a sample breath from a person not the driver, the sample air intake (211) should be placed within the compartment where a person occupying a sensing position may readily breathe into or closely adjacent the intake (211), and with the fresh air intake (209) again located to receive an air sample that will not include representative quantities of the breath exhalations of the person in the sensing position.

The output of the pump (201) connects through a forked pneumatic pathway (212) to the second and third valves (206 and 207). The second valve (206) connects to a pneumatic pathway (213) that leads to the input of the isolation unit (202). The third valve (207) allows the output of the pump (201) to be selectively provided to either the input of the isolation unit (202) or the input of the balance column (203).

The isolation unit (202) operates in accordance with the prior art principal of chromatography, and can be comprised of a quarter inch diameter aluminum tube having polarized carbon packed therein. Angel hair can be packed into both ends of the tube to aid in maintaining the content of the polarized carbon. Appropriate fittings can then be utilized to connect pneumatic pathways to either end of the isolation unit (202).

Figure 4:
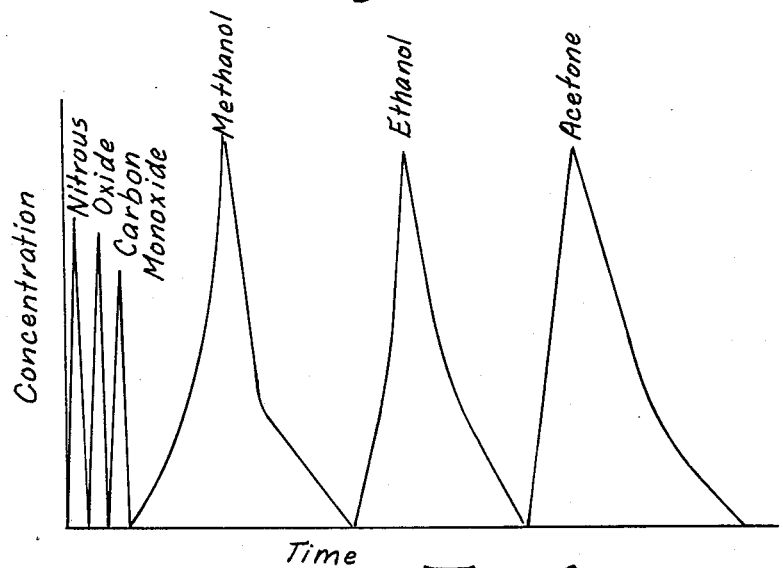
FIG. 4 comprises a graph depicting gas concentration levels versus time as output from the isolation unit this invention.

Briefly stated, a mixture of gases provided at the input of such a tube under constant pressure will be separately discharged on an isolated time flow basis. For instance, with reference to FIG. 4, a mixture of gases including nitrous oxide, carbon monoxide, methanol, ethanol, and acetone as provided to the input of such an isolation unit will exit from the isolation unit separated from one another in time. The nitrous oxide components will appear first, followed shortly by the carbon monoxide components. Later, methanol will appear, followed by the ethanol components, the latter being the gas of interest in this application.

The balance column (203) comprises a pneumatic pathway having baffle elements disposed therein, such as sand or glass or plastic beads, to aid in preventing sudden pressure variations from affecting operation of the sensor (214). To accomplish this, such baffle elements may preferably be of approximately the same mesh as the material in the isolation unit (202). Such balance columns are well understood in the art and hence no further detail need be set forth here.

The output of the isolation unit (202) connects to the fourth valve (208), which allows the isolation unit (202) to be selectively connected to either a first pneumatic pathway that leads to a first exhaust (216) or to a second pneumatic pathway leading to a second exhaust that includes the sensor (214). The output of the balance column (203) connects to the second exhaust in series with the sensor (214).

General operation of the pneumatic elements (200) of the this embodiment will now be described.

Upon being initiated, this embodiment operates in a warm-up mode for a period of time. In this mode, the pump (201) draws air through the fresh air intake (209) and provides it through the third valve (207) and balance column (203) to the sensor (214) and exhaust associated therewith.

Following the warm-up mode which can be eliminated with proper heat controls of the unit, the pump (201) operates for approximately thirty seconds to draw air through the sample air intake (211) and provide it through both the second and third valves (206 and 207) to the isolation unit (202). The fourth valve (208) in this operating mode provides the output of the isolation unit (202) to the first exhaust (216).

Following this, a comparison reference will be established by exposing the sensor (214) to the fresh air gas mixture as provided at the output of the pump (201) by allowing the third valve (207) to forward this mixture through the balance column (203) past the sensor (214). At the same time the second valve (206) continues to allow the fresh air gas mixture to be provided at the input of the isolation unit (202) and the fourth valve (208) continues to direct the output of the isolation unit to the first exhaust (216).

The third valve (207) will then again provide the pump (201) fresh air output to the intake of the isolation unit (202), and the fourth valve (208) will now provide the output of the isolation unit (202) to the sensor (214). Sufficient time will have passed such that the gases flowing from the isolation unit (202) will contain ethanol (if any ethanol existed in the original sample air mixture). The sensor (214) readings can then be interpreted to determine whether the original sample air mixture contained sufficient ethanol quantities to justify activation of the signal unit.

It will be noted, that unlike the conventional gas chromatograph arrangement where a pure gas is used as a carrier of the sample being tested, this system utilizes ambient air, i.e., the air from the fresh air intake (209) to carry the sample air from intake (211) through the gas chromatograph-tube isolation unit (202).

Finally, this embodiment conducts a purge operation for a given period of time. In this mode, the first valve (204) again draws air from the fresh air intake (209) and the second and third valves (206 and 207) allow this fresh air to be passed through both the isolation unit (202) and the balance column (203). In this way, residue gas mixtures can be cleansed from the system to prepare it for another cycle.

Figure 2:
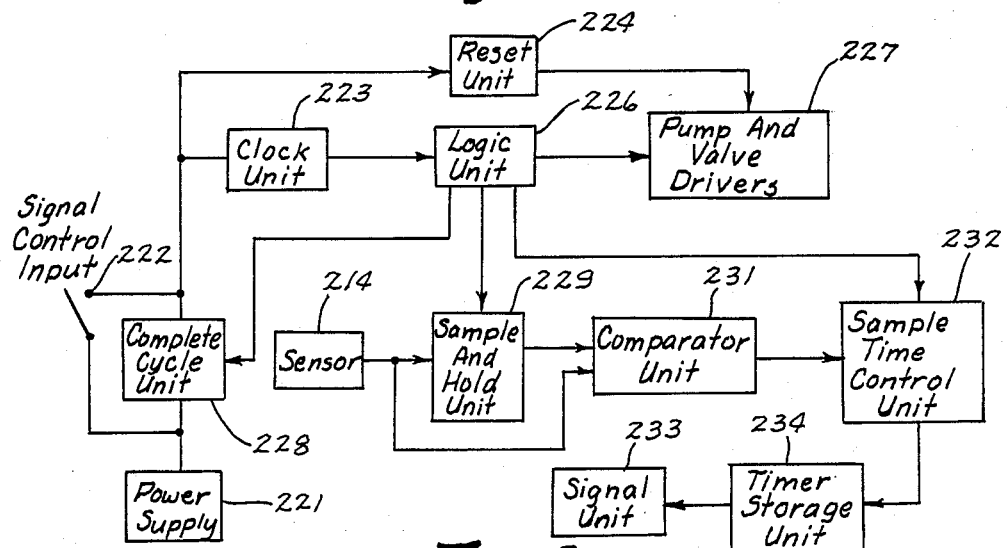
FIG. 2 comprises a block diagram view of the control therefor.

Various mechanisms can be utilized to control the timed operation of the valves (204, 206, 207 and 208) and pump (201). For instance, a simple electronic timer (not shown) has been designed for this system. More advantageously, electronics can be utilized to provide both the above noted timing functions and other features as well. A block diagram for such a system will now be described with reference to FIG. 2.

A power supply (221), such as a battery in the monitored vehicle (not shown), connects through a control signal input (222), such as an ignition switch, to a clock unit (223) and a reset unit (224). Closing the control signal input (222) will cause activation of the clock unit (223) and enablement of the reset unit (224). The clock unit (223) will provide clock pulses at a predetermined rate to a logic unit (226), which logic unit controls the timing of the pump and valve drivers indicated generally by the numeral 227. The reset unit (224) resets the pump and valve drivers (227) to effectively initiate operation of the control cycle.

In addition to controlling the sequencing of the pump and valve drivers (227), the logic unit (226) controls a cycle completion unit (228) that, when activated, causes the power supply (221) to remain connected to the clock unit (223) for a period of time to ensure completion of the entire pneumatic elements cycle described above even if the vehicle driver prematurely opens the ignition switch. This makes avoidance of the alcohol detecting function more difficult.

The gas sensor (214) connects to a sample and hold unit (229) and also to one input of a comparator (231). The sample and hold unit (229) has its output connected to the remaining input of the comparator (231). The sample and hold unit (229) is controlled by the logic unit (226), and will sample the output of the sensor (214) until caused by the logic unit (226) to hold that sensor output. The sample and hold unit (229) will then provide that held sensor output signal as a reference signal for the comparator (231) to use in detecting the presence of ethanol.

The output of the comparator (231) connects to a sample time control unit (232) that responds to the logic unit (226) to control when the output of the comparator (231) will be passed on to the signal unit (233).

Finally, a timed storage unit (234) will cause an alcohol-detected signal from the comparator (231) to be retained in a memory even if the ignition for the vehicle is switched off for a period of time. Upon restarting the vehicle under such circumstances (and within a relevant time frame, such as two minutes), the signal unit (233) would begin signalling in a non-standard pattern to thereby alert others of the potentially intoxicated condition of the driver. This feature also makes avoidance of the alcohol detecting function more difficult.

Figure 3A:
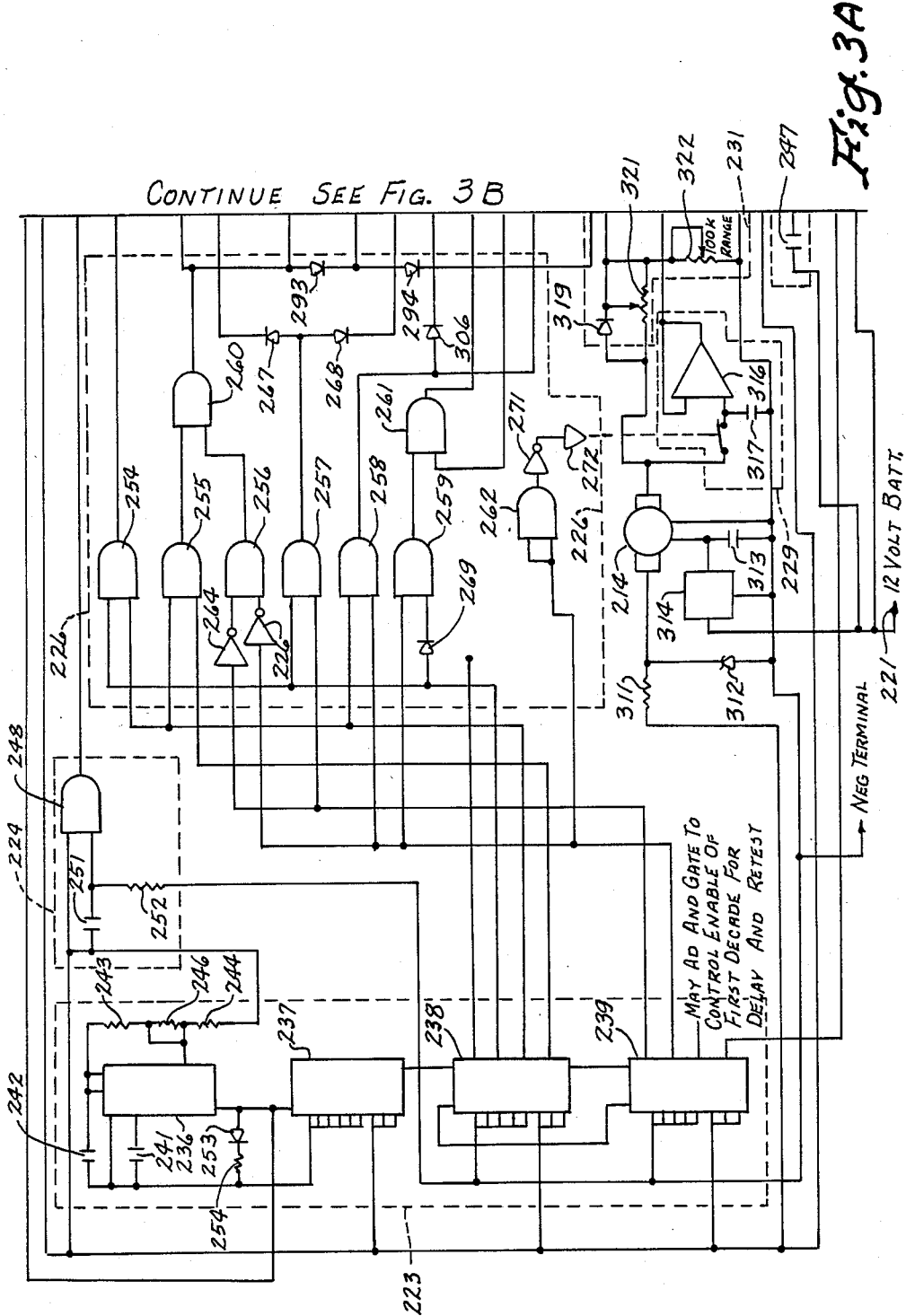
FIG. 3 comprises a schematic diagram of the control circuitry therefor.
Figure 3B:
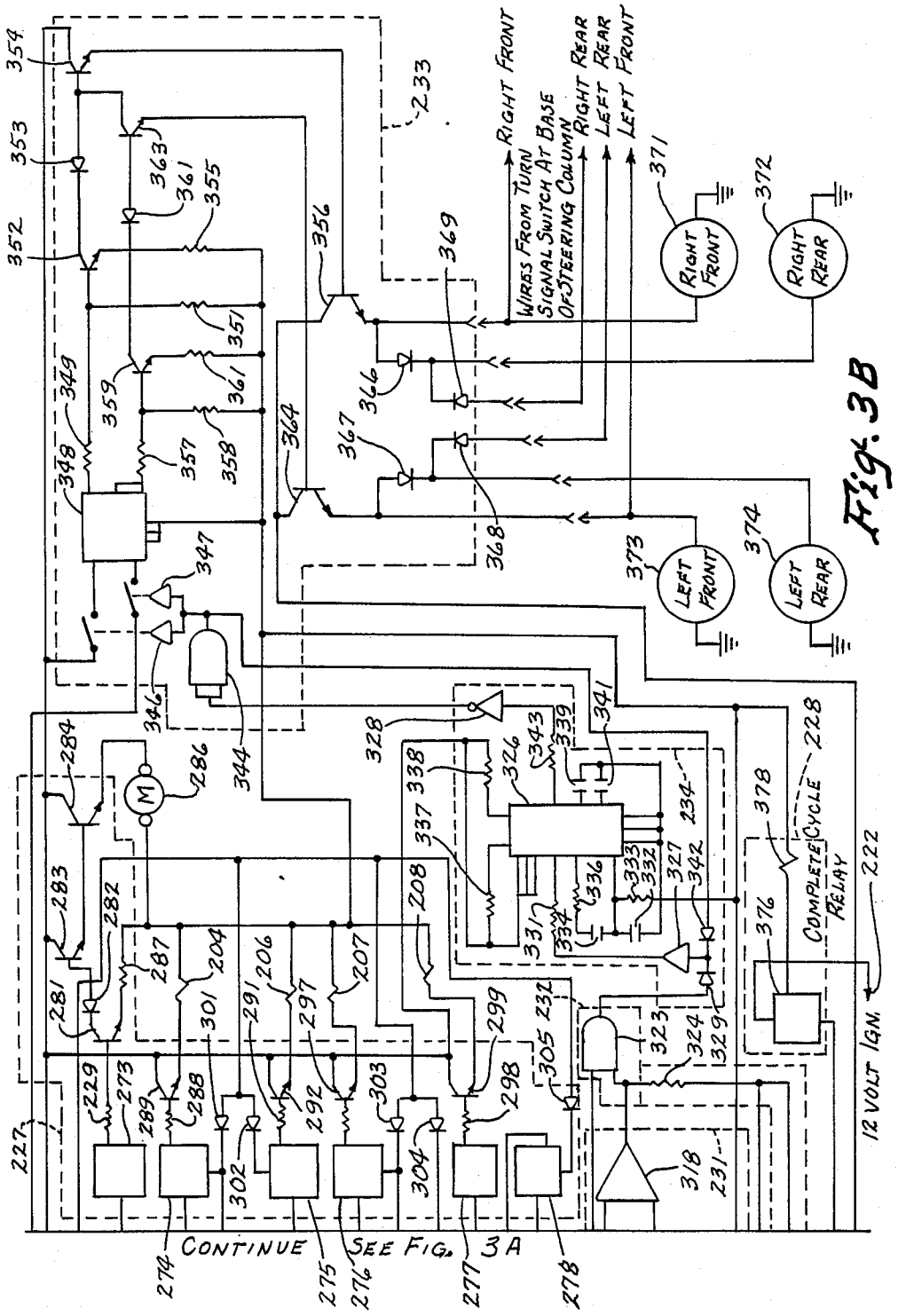

Referring now to FIG. 3, a more detailed description of an electronic circuit for appropriately controlling the pneumatic elements (200) of this embodiment will be described.

The clock unit (223) can be comprised generally of a 555 timer (236) and three 4029 decade counters (237, 238, and 239).

The 555 timer (236) has its ground input (pin 1) connected to ground and its control voltage port (pin 5) connected to a grounded 0.001 microfarad capacitor (241). The trigger and threshold ports (pins 2 and 6) are connected to a grounded 0.1 microfarad capacitor (242) and also to a resistor network comprised of two 1 mega ohm resistors (243 and 244) and a 1 mega ohm variable resistor (246). The variable leg and one terminal of the variable resistor (246) connect to the discharge port (pin 7) of the timer (236). The remaining side of the resistor network connects through a capacitor (247) to the power supply (221) and also to one input of a two input AND gate (248) that comprises the reset unit (224). The remaining input of this two input AND gate (248) connects through a 0.1 microfarad capacitor (251) to the resistor network mentioned above and through a 1 megaohm resistor (252) to ground.

The output port of the timer (236) connects through a series connected LED (253) and 1.5K ohm current limiting resistor (254) to ground and to the input port (pin 15) of the first decade counter (237) (which counter (237) has been configured as a divider). This decade counter (237) drives the second and third counters (238 and 239) (which counters are configured as counters), the outputs of which are connected to the logic unit (226) as described in more detail below.

The logic unit (226) includes nine two input AND gates (254–262) and assorted inverters and diodes. The first AND gate (254) has one input connected to pin 11 of the second clock unit decade counter (238). The remaining input to this AND gate connects to pin 14 of that same decade counter (238). The output of this AND gate (254) connects to the pump and valve drivers (227) as described below in more detail.

The second AND gate (225) has its first input connected to pin 14 of the first clock unit decade counter (238) and its second input connected to pin 2 of that same counter (238). The output of this second AND gate (225) connects to one input of the seventh AND gate (260).

The third AND gate (256) has one input connected via an inverter (264) to pin 6 of the third decade counter (239). The remaining input to this AND gate (256) similarly connects through an inverter (266) to pin 11 of the same decade counter (239). The output of this AND gate (256) connects to the remaining input of the seventh AND gate (260). (The output of the seventh AND gate connects to the pump and valve drivers (227) as described below in more detail.)

The fourth AND gate (257) has a first input connected to pin 11 of the second decade counter (238) and a second input that connects to pin 6 of the third decade counter (239). The fourth AND gate (257) connects to the pump and valve drivers (227) through a pair of diodes (267 and 268) as described below in more detail.

The fifth AND gate (258) has a first input connected to pin 14 of the second decade counter (238) and a second input that connects to pin 11 of the third decade counter (239). The output of this AND gate (258) connects to the pump and valve drivers (227) as described below in more detail.

The sixth AND gate (259) has a first input that connects to pin 11 of the third decade counter (239) and a remaining input that connects through a forward biased diode (269) to pin 11 of the second decade counter (238). The output of this AND gate (259) connects to one input of the eighth AND gate (261), the remaining input and the output of which connect to the pump and valve drivers (227) as described below in more detail.

Finally, the ninth AND gate (262) has both inputs connected in common to pin 11 of the third decade counter (239). The output of this AND gate (262) connects through an inverter (271) to a bi-lateral switch (272) as provided through use of a 4016. This bi-lateral switch (272) controls a line of conductivity in the sample and hold unit (229) as described below in more detail.

The pump and valve drivers (227) can be comprised of six flip-flops (273–278) and a number of drive transistors. The first flip-flop (273) has its set port connected to the output of the first logic unit AND gate (254). The Q-output port of this flip-flop (273) connects through a 100 ohm resistor (279) to the base of a 2N222A transistor (281), the collector of which connects through a diode (282) to the base of a SK3025 PNP transistor (283). The emitter of the latter (283) connects to the power supply (221) and the collector connects to the base of a second 2N222A transistor (284). The emitter of the latter (284) connects to one side of a pump motor (286) for the pump (201) described above. The remaining terminal of the pump motor (286) connects through a 10K ohm resistor (287) to the emitter of the first 2N222A transistor (281) and to ground. So configured, the first flip-flop (273) can control the operational status of the pump motor (286) through appropriate switching of the above noted transistors (281, 283 and 284).

The second flip-flop (274) has its set port connected to the output of the seventh logic unit AND gate (260). The Q-output port connects through a 1K ohm resistor (288) to the base of a first 2N3904 transistor (289), the collector of which connects to the power supply (221) and the emitter of which connects to the first valve (204). So configured, the second flip-flop (274) can control the operational status of the first valve (204) and hence can control whether fresh air or sample air is provided to the pump (201).

The third flip-flop (275) has its set input connected to also receive the output of the seventh logic unit AND gate (260). The Q-output port for this flip-flop (275) connects through a 1K ohm resistor (291) to the base of another 2N3904 transistor (292), the collector of which connects to the power supply (221) and the emitter of which connects to energize and control the second valve (206). So configured, the third flip-flop (275) can control the operational status of the second valve (206) to thereby control when the pump (201) provides output to the isolation unit (202) (depending also, of course, upon the operational status of the third valve (207)).

The fourth flip-flop (276) has its set input connected through a forward biased diode (293) to the output of the seventh logic unit AND gate (260) and also through another forward biased diode (294) to the output of the eighth logic unit AND gate (261). Hence, either of these AND gates (260 and 261) can set the fourth flip-flop (276). The Q-output port for this flip-flop (276) connects through a 1K ohm resistor (296) to the base of another 2N3904 transistor (297), the collector of which connects to the power supply (221) and the emitter of which connects to control functioning of the third valve (207). So configured, the fourth flip-flop (276) can control the operating status of the third valve (207) to control the provision of the pump output to the isolation unit (202) and the balance column (203).

The fifth flip-flop (277) has its set input connected to the output of the eighth logic unit AND gate (261) and its Q-output connected through a 1K ohm resistor (298) to the base of another 2N3904 transistor (299), the collector of which connects to the power supply (221) and the emitter of which connects to control the fourth valve (208). So configured, the flip-flop (277) can control the operational status of the fourth valve (208) to thereby control whether the output of the isolation unit (202) flows to the first exhaust (216) or to the sensor (214).

The sixth flip-flop (268) has its set input connected to receive the output of the fifth logic unit AND gate (258). Its Q-output port connects back to one input of the eighth logic unit AND gate (261). In this way, the sixth flip-flop (278) controls, in part, the output of the eighth AND gate (261) to thereby control to some extent setting of the fourth and fifth flip-flops (276 and 277).

The reset unit AND gate (248) described earlier provides a reset signal directly to the reset port of the first flip-flop (273) and through appropriate diodes (301–305) to the reset ports of the second through sixth flip-flops (274–278). In addition, the output of the fourth logic unit AND gate (257) connects through an earlier mentioned diode (267) to the reset port of the second flip-flop (274), and through another earlier mentioned diode (268) to the reset port of the fourth flip-flop (276) to provide an alternative mechanism for resetting the second and fourth flip-flops (274 and 276). Similarly, the output of the fifth logic unit AND gate (258) connects through a diode (306) to the reset port of the fifth flip-flop (277) to provide an alternative mechanism for resetting this flip-flop (277).

The sensor (214) can again be comprised of a solid state gas sensor such as a TGS812 as described with respect to the first embodiment. The input ports of the sensor (214) connect through a 470 ohm resistor (311) to the power supply (221). The input to the sensor (214) also connects to a 9.1 volt Zener diode (312). One heater terminal for the sensor (214) connects to ground and the remaining heater terminal connects to a 0.05 farad capacitor (313) and to the output of a 5 volt regulator (314). So configured, the sensor (214) can provide output signals to both the sample and hold unit (229) and the comparator (231).

The sample and hold unit (229) includes a 3130 operational amplifier (316) and a 0.1 microfarad grounded capacitor (317). The non-inverting input of the operational amplifier (316) connects to the grounded capacitor (317) and through a switch contact controlled by the logic unit bi-lateral switch (272) to the output of the sensor (214). The output of the operational amplifier (316) connects to the inverting input thereof and also to the comparator (231) as described below.

The comparator (231) includes a 339 comparator (318), a diode (319), and a 10K ohm and a 100K ohm variable resistor (321 and 322). The output of the sample and hold operational amplifier (316) connects to one input of the comparator (318). The remaining comparator input connects to the grounded 100K ohm variable resistor (322) and through the parallel connected diode (319) and 10K ohm resistor (321) to the output of the sensor (214). So configured, the comparator (318) will provide an output to the sample time control unit (232) that reflects the difference between the output of the sample and hold unit (229) and the sensor output.

The sample time control unit (232) can be comprised of a two input AND gate (323). One input of this AND gate (323) receives the output of the eighth logic unit AND gate (261). The remaining AND gate input connects to a biasing 10K ohm resistor (324) and also to the output of the comparator (318). So configured, the sample time control unit (232) will provide an output signal to the timed storage unit (234) when both the comparator unit (231) and the eighth logic unit AND gate (261) provide a high output. (348) to the power supply (221). The second bi-lateral switch (347) connects a control voltage input of this same 556 timer (348) to the output of the clock unit timer (236). The reset port and the trigger port for this 556 timer (348) connect to ground. The discharge port connects through a 1K ohm resistor (349) to a grounded 1K ohm resistor (351) and the base of a first SK3025 transistor (352). The collector of this transistor (352) connects through a switching diode (353) to the base of a second SK3025 transistor (354), the emitter of which connects to the power supply (221) and the collector of which connects to a first 2N3772 transistor (356). The output and threshold ports of the 556 timer (348) connect through a 1K ohm resistor (357) to a grounded 1K ohm resistor (358) and the base of a third SK3024 transistor (359). The emitter of this transistor connects to a grounded 10K ohm resistor (361). The collector connects through a switching diode (362) to the base of an SK3025 PNP transistor (363), the emitter of which connects to the power supply (221) and the collector of which connects to the base of a second 2N3772 transistor (364).

The collectors of both 2N3772 transistors (356 and 364) are connected to the power supply (221) and the emitters connect to a diode and light network. More particularly, the emitter of the first transistor (356) connects directly to a right front signal light of the vehicle and through a diode (366) to a right rear signal light. The emitter of the second transistor (364) connects to a left front signal light and through another diode (367) to a left rear signal light. Additional diodes (368 and 369) are provided to allow conventional operation of these signal lights (371-374).

The timed storage unit (234) includes a 556 timer (326), two inverters (327 and 328) and a number of resistors, capacitors and diodes. The output of the sample time control unit (232) connects through a series connected diode (329), inverter (327), and 1K ohm resistor (331) to one trigger input (pin 6) of the timer (326). The remaining trigger input (pin 8) connects to a grounded parallel combined 10 microfarad capacitor (332) and 10 megaohm resistor (333), and also through a series connected diode (334) and 10K ohm resistor (336) to one output thereof. Both discharge ports (pins 1 and 13) and the ground port (pin 7) connect to ground. Both theshold ports (pins 2 and 12) connect to the power supply (221) through 10K ohm resistors (337 and 338). Both reset ports (pins 4 and 10) and the $V_{cc}$ port (pin 14) are connected to the power supply (221). The control voltage ports (pins 3 and 11) connect to ground through 0.001 microfarad capacitors (339 and 341).

The first trigger input (pin 6) can also be enabled through a diode (342) by the signal unit (234) as described below in more detail. Finally, the second output (pin 9) connects through a 1K ohm resistor (343) and inverter (328) to both inputs of a two input AND gate (344) that comprises the input of the signal unit (233). So configured, the timed storage unit (234), once triggered by the comparator unit (231) via the sample time control unit (232), will serve to provide an enabling output signal to the signal unit (233) for a lengthy period of time, even upon switching off the ignition switch.

The output of the AND gate (344) connects to trigger the 556 timer (326) of the timed storage unit (234) and also connects to trigger two bi-lateral switches (346 and 347). The first bi-lateral switch (346) connects the $V_{cc}$ port of a 556 timer Finally, the cycle completion unit (228) includes a 556 timer (376), the reset port of which connects to receive an output of the third clock unit decade counter (239) and the trigger input of which connects to the control signal input (222). The discharge port for this timer (376) connects to an enabling relay (378) that serves to connect the circuitry to the battery even if the ignition switch (222) is subsequently switched off.

General operation of the control circuitry will now be described. Upon initiating the vehicle's ignition, the cycle completion unit (228) closes the enabling relay (378) to ensure adequate time and power for the second embodiment to complete its gas analysis cycle. At the same time, the reset unit (224) receives an enabling pulse that causes it to reset all of the flip-flops in the pump and valve drivers (227). Further, closing the ignition triggers the clock unit (223) to cause an incremental advance of triggering output pulses that effectuate sequential logic processing in the logic unit (226). The logic unit (226) in turn, provides for sequential operation of the pump and valve driver flip-flops to thereby cause appropriate operation of the pump motor (286) and the four valves (204, 206, 207 and 208) to effectuate operation of the pneumatic elements (200) as described above.

As the pneumatic elements (200) operate, the sensor (214) continually provides an output signal to the sample and hold unit (229) and the comparator (231). Any difference noted by the comparator unit (231) between these two signals will not be subsequently processed due to non-enabling of the sample time control unit (232).

At a relevant time in processing, the logic unit (226) will cause the bi-lateral switch (272) associated therewith to open the input line between the sensor output and the sample and hold unit operational amplifier (316). When this occurs, the input to this operational amplifier (316) will be a function of the voltage across the capacitor (317) connected thereto. In effect, this operational amplifier (316) will be providing at its output the sensor output as of the time the bi-lateral switch (272) opens.

Shortly following this, the sensor (214) will be exposed to the ethanol gas as isolated in the isolation unit (202). This reading can then be compared by the comparator unit (231) with the held sample sensor output as provided by the sample and hold unit (229). If a requisite quantity of ethanol appears in the sample gas, the comparator unit (231) will provide a positive output.

The sample time control unit (232) will be enabled at the correct time by the logic unit (226) to allow passage of this ethanol detected signal to the timed storage unit (234). The timed storage unit (234) will then provide an enabling signal to the signal unit (233). This signal will be provided by the timed storage unit (234) even if the ignition is now shut off. Provided that the ignition is re-closed within a few minutes, the signal unit (233) will still be causing appropriate non-standard operation of the signal lights (371-374) to warn those around the vehicle of the potentially intoxicated state of the driver located therein.

FIG. 5 illustrates a vehicle apparatus for assisting the operation of the suction pump (201) in withdrawing the driver's exhalation for sampling purposes thereof, should such assistance be necessary. The apparatus depicts a vehicle dashboard (400) through which a steering column (401) extends, and showing a steering wheel (402), with a conventional firewall (403) mounted between the dashboard (400) and the interior (404) of the vehicle's engine compartment.

Under certain conditions, the suction pump (201) is connected by a pneumatic tube (406) to the first valve (204) (see also FIG. 1) for effecting the drawing of both fresh air from a fresh air intake (209) mounted interior the vehicle passenger compartment as described hereinbefore; and further the pump (201) operates via the first valve (204), being operated in timed sequence as all so described hereinbefore, to draw into the system the driver's exhalation through the sample air intake (211) mounted on the steering column (401) behind the steering wheel (402), via a pneumatic tube (407). In this condition, the intake end (408) of the tube (407) would be connected to the sample air intake (211), rather than as shown herein.

Should it be desirable to assist the suction operation of the pump (201), a one liter mixing container (409) is mounted in the interior (404) of the engine compartment and to which the sample tube end (408) is fluidly connected. The container (409) is further connected by a tube (411) to the sample air intake (211), and by another tube (412) and a T-fitting (413) into a suction line (414) of the vehicle's conventional pneumatic exhaust system. A flow control valve (416) is interposed in the tube (412), controlled by appropriate timed operation of the clock unit (223) (FIG. 2) to function in timed sequence with operation of the first valve (204) to ensure sufficient suction is present at the sample air intake (211) to draw the driver's exhalation into the container (409), and to hold same there sufficiently to obtain a representative sample of said exhalation.

In use, this embodiment will cause all exterior lights on the vehicle except headlamps to operate in a non-standard fashion when the gas sensor (214) detects an inappropriate level of alcohol.

It may be desirable to detect a level or value of any gas using this system as described hereinbefore, and wherein the system is taken out of the vehicle. In this arrangement, the sample air intake (211) is placed in the environment of the gas to be sensed, and the fresh air intake (209) is again located to receive an air sample, i.e., ambient air, that is not likely to include representative quantities of the gas the value of which is being sensed. The remainder of the system, its components and operation as described and illustrated hereinbefore remain the same.

Figure 6:
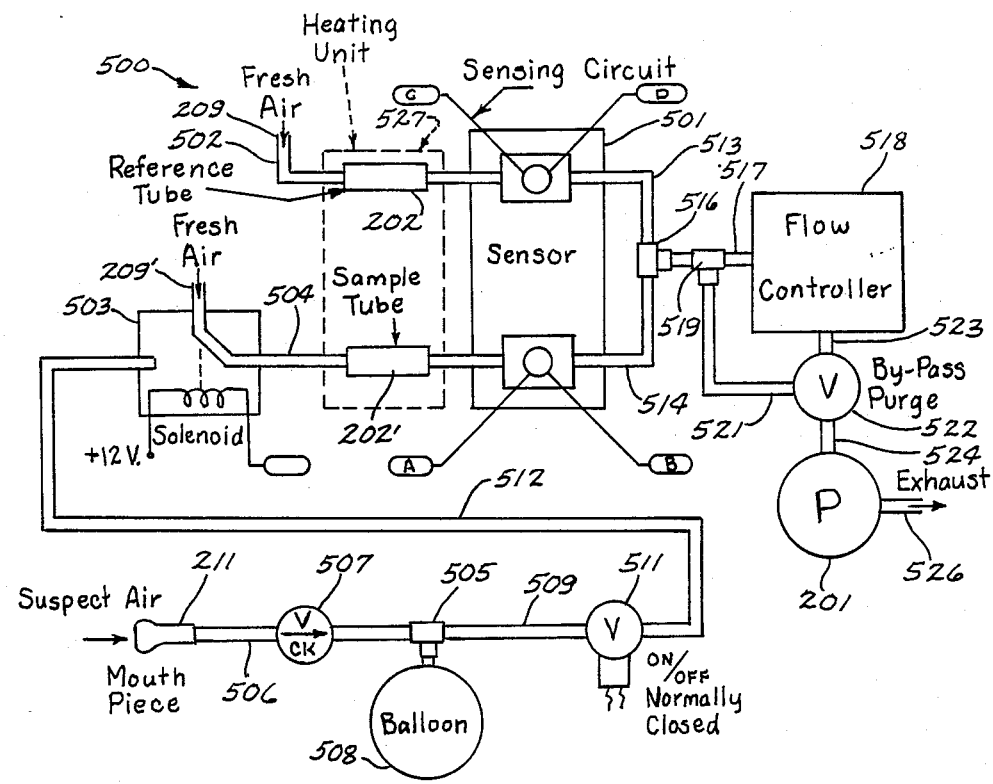
FIG. 6 is a schematic illustrating a modified gaseous detection system of this invention.

FIG. 6 discloses a further modification of the breath analyzer apparatus of this invention comprising a sensor unit (501) the conventional circuit (not shown) which includes a Wheatstone bridge for measuring the electrical resistances of two paths of gas mixture or air flow, the results of which are compared in a manner similar to that of the previously described embodiments with a resulting signal to be used as desired by the operator of the apparatus.

The first path comprises a fresh air intake (209) leading through a conduit (502) to an isolation unit (202) and thence operably connected to the sensor unit (501) wherein the profile of the gas chromatographic reference tube is applied as by generating an electric current to one side of the Wheatstone bridge.

The second path of gas mixture or air flow includes a pair of sub-paths both leading to a solenoid controlled valve unit (503). The first sub-path comprises another fresh air intake (209') leading through the valve unit (503), when the latter is controlled by a conventional control circuit to be open to the fresh air intake (209') to a second isolation unit (202') and thence operably connected to the sensor unit (501) wherein the profile of this gas chromatographic sample tube is applied as by generating an electric current to the other side of the Wheatstone bridge. It will be noted that the makeup and operation of the isolation units (202), (202') are the same as previously described hereinbefore.

The second sub-path comprises a path of sample or suspect air initiated at a mouthpiece (211) connected through a conduit (506) to a one-way check valve (507) and then to a balloon (508) of predetermined capacity through a conduit (509) to a normally closed check valve (511), and thence through another conduit (512) to the valve unit (503). With the latter unit (503) open only to the conduit (512), the suspect air is transmitted through the isolation unit (202') wherein again a profile of the gas mixture from conduit (512) generates an electric current which is then applied to the same side of the Wheatstone bridge as the current generated from fresh air through the first sub-path.

From the sensor unit (501), the gas mixture or air flow of the isolation units (202) and (202') is conducted through conduits (513), (514), respectively, to a T (516), and from there through a conduit (517) to a flow control unit (518) of conventional design the purpose of which is to provide a constant flow of gas mixture in both units (202) and (202') regardless of the type of gas, fresh air or suspect air, passing through same.

The conduit (517) is fluid connected by a T (519) via a conduit (521) to a by-pass purge valve (522) connected by conduits (523), (524), respectively, in turn to the flow control unit (518) and to a pump (201) comparable to that of the FIG. 1 embodiment and with the pump (201) having an exhaust (526).

A conventional heating unit is illustrated by dotted lines at (527) to encompass both isolation units (202) and (202') for maintaining them at a constant predetermined temperature thus obviating the need for any warm-up procedure step as described hereinbefore. Further, it is contemplated that the entire apparatus of FIG. 6 may be heated to ensure the uniform flow of gases. Additionally, with the isolation unit (202') operating in accordance with the principal of gas chromatography, the isolation unit (202) need not be identical, but must have the same flow characteristics.

As mentioned hereinbefore with respect to the apparatus of FIG. 6, appropriate conventional circuits are provided for supplying electric power to drive the apparatus (500), for heating the appropriate elements, for timing the operation of all elements, and for deriving a signal from the sensor unit (501), all as described hereinbefore with respect to the first embodiment. Use of the signal is optional: an opening of a vehicle ignition system such that an inebriated operator cannot operate the vehicle; an operation of vehicle standard lights in a non-standard manner; the provision of a visual display or print-out of the amount of ethanol or any other specified gas in the sample of gas mixture blown or sucked into the mouthpiece (211) and into the balloon (508).

One operation of the apparatus (500) of FIG. 6 is initiated by a police officer for example, turning the apparatus (500) on, the apparatus being powered by a 12 volt source. Initially, the pump (201) operates to pull the fresh air through both conduits (502) and (504) and through the isolation units (202) and (202') to the sensor unit (501), and through the conduits (513), (514), (521), and (524) to exhaust (526). This also permits the heater (527) to bring the units (202), (202') up to a desired operating temperature, a light (not shown) being available if desired to indicate that the operating temperature is attained.

The officer then instructs the suspect person to blow into the mouthpiece (211) to fill the balloon (508), the suspect then ceases blowing and the officer presses a conventional "start" button for the apparatus (500), such action initiating the conventional operational timing sequence of the system (500). The pressing of the "start" button provides for activation of the Wheatstone bridge and comparative circuits to obtain a base line evaluation from the passage through the sensor unit (501) of fresh air from both gas mixture paths of isolation units (202), (202'); such base line evaluation being a zero reading for example, on an L.C.D. display or printed tape (not shown). This provides a blank test wherein a zero reading should result.

The timing circuit then operates to open the valve (511) and to switch the solenoid valve unit (503) such that suspect air from the balloon (508) rather than fresh air from (209') is transmitted under vacuum pressure from the pump (201) through the lower isolation unit (202') and into the sensor unit (501) for a predetermined period of time, thereby unbalancing the Wheatstone bridge arrangement, assuming ethanol to be present in the suspect air, which unbalanced bridge provides a changed signal from the comparator unit, resulting in a new reading as indicated on the L.C.D. display or print-out. If no ethanol is present in the suspect air from the balloon (508), an output signal reading of zero would again indicate the absence of ethanol.

The apparatus (500) then automatically returns to a purge situation; valve (511) closing, solenoid valve (503) closing off conduit (512) and opening the conduit (504) to the fresh air input (209') such that fresh air is again being pulled not only through isolation unit (202) but again through isolation unit (202'). With both isolation units (202), (202') carrying fresh air, the signal resulting from an again balanced Wheatstone bridge should again be a zero reading.

The conventional timing circuit then turns off the heating unit and operates the pump (201) to purge the pneumatic elements of the apparatus (500) of any and all traces of suspect air. The apparatus is then ready for the next test.

The purge valve (522) may be activated by a special timing sequence or operation, if desired, to by-pass the flow control unit (518) and to rapidly purge the entire pneumatic system and apparatus (500) of all suspect air such that the apparatus (500) is made ready for the next test.

Obviously, numerous modifications and variations of the present invention are possible in light of the above teachings. It is to be specifically understood that it will be possible to vary the values of units to sense predetermined levels of almost any gas in almost any environment and to signal the level sensed. It is therefore to be understood, that within the scope of the appended claims, the invention may be practiced otherwise than as specifically described therein.

We claim:

1. A gas detection system for detecting the presence of and determining the level of a preselected gas, the system comprising:
   (a) sensing means for sensing the preselected gas, said sensing means including isolation means having an input for receiving a mixture of gases at a substantially constant pressure, and an output for providing a sequential flow of substantially segregated gases, such that the preselected gas as contained within said mixture of gases will be provided in substantially isolated form at said output during a preselected window of time following introduction of said mixture of gases to said input;
   (b) means for providing a signal when said preselected gas is sensed;
   wherein said sensing means further includes:
   a first exhaust outlet;
   a second exhaust outlet; and
   first valve means operably connected to said isolation means and said first and second exhaust outlets for selectively connecting said output of said isolation means to said first and second exhaust outlets.

2. The system of claim 1 wherein said sensing means further includes a sensor responsive to preselected gas and which provides an electric signal in response thereto, said sensor being pneumatically connected in series with said second exhaust outlet.

3. A gas detection system for detecting the presence of and determining the level of a preselected gas, the system comprising:
  (a) sensing means for sensing the preselected gas, said sensing means including isolation means having an input for receiving a mixture of gases at a substantially constant pressure, and an output for providing a sequential flow of substantially segregated gases, such that the preselected gas as contained within said mixture of gases will be provided in substantially isolated form at said output during a preselected window of time following introduction of said mixture of gases to said input;
  (b) means for providing a signal when said preselected gas is sensed;
  wherein said sensing means further includes:
  a sensor responsive to preselected gas and which provides an electric signal in response thereto;
  a first pneumatic pathway connected in series with said sensor;
  a second pneumatic pathway connected in parallel to said first pathway with said sensor; and
  valve means for controlling said sequential flow of substantially segregated gases from said isolation means with respect to said first and second pneumatic pathways.

4. The system of claim 1 wherein said sensing means further includes suspect air intake means positioned to receive said preselected gas samples.

5. The system of claim 4 wherein said sensing means further includes fresh air intake means positioned to receive air not likely to include said preselected gas.

6. The device of claim 5 wherein said sensing means further includes:
  a pneumatic pathway; and
  valve means for controlling a flow of gas samples from said suspect air intake means and said fresh air intake means into said pneumatic pathway.

7. The system of claim 6 wherein said sensing means further includes pump means for drawing a flow of gases through said pneumatic pathway and valve means from said fresh air intake means and said suspect air intake means.

8. The system of claim 1 wherein said isolation means includes a pneumatic pathway having polarized carbon disposed therein.

9. A gas detection system for detecting the presence of and determining the level of a preselected gas, the system comprising:
  (a) sensing means for sensing the preselected gas, said sensing means including isolation means having an input for receiving a mixture of gases at a substantially constant pressure, and an output for providing a sequential flow of substantially segregated gases, such that the preselected gas as contained with said mixture of gases will be provided in substantially isolated form at said output during a preselected window of time following introduction of said mixture of gases to said input;
  (b) means for providing a signal when said preselected gas is sensed;
  wherein said sensing means includes:
  a sensor for providing an electronic signal in response to being exposed to gases of interest;
  comparator means for comparing an output of said sensor with a reference value to determine presence of said gases of interest; and
  sample and hold means for forming said reference value as a function of said sensor's output.

10. The system of claim 9 wherein said sample and hold means receives said output of said sensor during a period of time when said sensor is not likely to be exposed to said gas of interest, and bases said reference value thereon.

11. The system of claim 10 and further including cycle completion means for causing said system to maintain said sensing means in an enabled state once enabled for at least a predetermined period of time.

12. The system of claim 11 further including storage means for storing said signal for at least a preselected period of time.

13. (twice amended) A gas detection system for detecting the presence of and determining the level of a preselected gas, the system comprising:
  (a) sample means for obtaining samples of both ambient air, and suspect air possibly containing a preselected gas;
  (b) isolation means for receiving said suspect air from said sample means and substantially isolating the preselected gas at a substantially constant pressure from other gases therein, said isolation means subsequently receiving said ambient air from said sample means;
  (c) means for receiving ambient air from said sample means at the same time as said isolation means receiving said ambient air sample, whereby to obtain a reference value;
  (d) means for sensing said reference value; and
  (e) signal means for providing a signal in response to the sensing of said isolated preselected gas.

14. The system of claim 13 wherein said sensing means further includes a first element having polarized carbon packed therein, and pump means for transmitting sample air to said first element at a constant pressure for passage therethrough.

15. The system of claim 14 wherein said sensing means further includes a second element having flow inhibiting material packed therein placed in parallel with said first element for preventing surges of ambient air from being transmitted to said sensing means.

16. The system of claim 14 wherein said sensing means further includes a plurality of valves whereby ambient air is transmitted to said first element subsequent to transmission thereto of said suspect air for purging said first element.

17. A method of detecting a preselected gas comprising the following steps:
  (a) sampling and measuring ambient air to create a first reference value;
  (b) sampling suspect air;
  (c) isolating a preselected gas, if present, from said sampled suspect air and measuring said isolated gas to create a second reference value;
  (d) comparing said isolated gas second reference value with said ambient air first reference value;
  (e) sensing the level of said isolated gas; and
  (f) generating a signal in response to said isolated gas level.

18. The method of claim 17 and further including the step of transmitting said suspect air at a known time flow rate for detecting the preselected gas therein.

19. The method of claim 18 and further including the step of timing the sensing of said suspect air in relation to the known time flow rate for said preselected gas.

20. The method of claim 17 and further including the step of forcing said suspect air into an isolating element at a predetermined pressure level.

21. The method of claim 17 and further including the step of ensuring the accuracy of said sensing device reading the level of said isolated gas by timing said reading on an isolated time flow basis subsequent to the step of forcing said suspect air into said isolating element.

22. The method of claim 17 and further including the step of forcing said suspect air into a chromatograph tube at a predetermined pressure.

23. A method of detecting a preselected gas comprising the following steps:
(a) sampling a first gas and generating a first reading therefrom;
(b) sampling a first gas and generating a second reading therefrom;
(c) comparing said first and second readings and obtaining a first evaluation therefrom;
(d) sampling a suspect gas possibly containing said preselected gas and generating a third reading therefrom;
(e) comparing said first and third readings and obtaining a second evaluation therefrom; and
(f) generating a signal from said second evaluation.

24. The method of claim 23 and further wherein said first and second readings comparison occurs simultaneously.

25. The method of claim 24 and further wherein said first and third readings comparison occurs simultaneously.

26. The method of claim 25 and further wherein said suspect gas sampling includes obtaining a profile of said suspect gas, isolating said preselected gas if found within said profile on a timed basis, and generating a current from said preselected gas isolated profile for use as a third reading.

27. An ethanol detection system for use in a vehicle having an interior compartment, the system comprising:
(a) sensing means for sensing ethanol in the breath of an selected individual in gaseous form in said interior compartment of said motor vehicle and said sensing means including isolation means for having an input for receiving a mixture of gases from said interior compartment at a substantially constant pressure, and an output for providing a sequential flow of substantially segregated gases, such that ethanol gas as contained within said mixture of gases will be provided in substantially isolated form at said output during a preselected window of time following introduction of said mixture of gases to said input;
(b) actuation means for providing an actuation signal when said sensed ethanol at least exceeds a preselected concentration level;
wherein said sensing means further includes:
a first exhaust outlet;
a second exhaust outlet; and
a first valve means operably connected to said isolation means and said first and second exhaust outlets for selectively connecting said output of said isolation means to said first and second exhaust outlets.

28. The system of claim 27 and further including signal means responsive to said actuation signal for causing a plurality of lights on said vehicle to alternatively ignite and extinguish in a substantially non-standard pattern.

29. The system of claim 27 wherein said sensing means further includes a sensor responsive to gaseous ethanol and which provides an electric signal in response thereto, said sensor being pneumatically connected in series with said second exhaust outlet.

30. The system of claim 27 wherein said sensing means further includes:
a sensor responsive to gaseous ethanol and which provides an electrical signal in response thereto;
a first pneumatic pathway connected in series with said sensor;
a second pneumatic pathway connected in parallel to said first pathway with said sensor; and
valve means for controlling said sequential flow of substantially segregated gases from said isolation means with respect to said first and second pneumatic pathways.

31. The system of claim 27 wherein said sensing means further includes sample air intake means positioned within said interior compartment to likely receive therein gas samples of breath exhalations of a person occupying a driving position in said vehicle.

32. The system of claim 31 wherein said sensing means further includes fresh air intake means positioned to likely receive therein gas samples that are not substantially representative of breath exhalations of a person occupying a driving position in said vehicle.

33. The device of claim 32 wherein said sensing means further includes:
a pneumatic pathway; and
valve means for controlling a flow of gas samples from said sample air intake means and said fresh air intake means into said pneumatic pathway.

34. The system of claim 33 wherein said sensing means further includes pump means for drawing a flow of gases through said pneumatic pathway and valve means from said fresh air intake means and said sample air intake means.

35. The system of claim 34 and further wherein said pneumatic pathway includes a pneumatic container interconnected between said sample air intake means and the exhaust system of the vehicle, with said pump means fluidly connected to said container for withdrawing said sample air therefrom, and with flow control valve means fluidly interposed in said pathway between said container and the exhaust system for controlling the suction therethrough of said sample air.

36. The system of claim 27 wherein said isolation means includes a pneumatic pathway having polarized carbon disposed therein.

37. The system of claim 27 wherein said sensing means includes:
a sensor for providing an electronic signal in response to being exposed to gases of interest;
comparator means for comparing an output of said sensor with a reference value to determine presence of said gases of interest; and
sample and hold means for forming said reference value as a function of said sensor's output.

38. The system of claim 37 wherein said sample and hold means receives said output of said sensor during a period of time when said sensor is not likely to be exposed to said gas of interest, and bases said reference value thereon.

39. The system of claim 27 wherein:
said vehicle has an ignition system; and
said system is enabled by initiation of said ignition system.

40. The system of claim 39 and further including cycle completion means for causing said system to maintain said sensing means in an enabled state once enabled for at least a predetermined period of time, even if said ignition system is subsequently switched off.

41. The system of claim 40 wherein said actuation means further includes storage means for storing said actuation signal for at least a preselected period of time, even if said ignition system is switched off.

42. A system for detecting the presence and level of a preselected gas, the system comprising:
a first pneumatic pathway for transmitting a first gas;
a second pneumatic pathway for transmitting either a first gas or a gas suspected of containing the preselected gas;
first means for developing a profile of said first gas;
second means for developing a profile of either said first gas or of said suspect gas;
sensor means for simultaneously evaluating and comparing said first gas from both said first and second pathways and generating a first reading therefrom, said sensor means subsequently evaluating and comparing said first gas from said first pathway with said suspect gas from said second pathway and generating a second reading therefrom; and
means responsive to said first reading and to said second reading for generating indicia of the presence and level of said preselected gas.

43. The system of claim 42 wherein flow control means is provided for maintaining a constant flow of said gases throughout said system.

44. The system of claim 43 wherein heating means is provided for maintaining said system under a predetermined temperature.

45. The system of claim 42 wherein isolation means if provided in each pneumatic pathway for generating a first profile of said first gas being transmitted therethrough, and for generating a second profile of suspect gas being transmitted therethrough, and for generating a first current from said first profile and a second current from said second profile for comparison purposes of said first and second currents.

46. The system of claim 45 wherein said sensor means includes a Wheatstone bridge, and wherein said first current of said first pathway is applied to one leg of said bridge and said first current of said second pathway is simultaneously applied to the other leg of said bridge for obtaining a first reading, and wherein subsequently said first current of said first pathway is applied to one leg of said bridge and simultaneously said second current is applied to the said other leg of said bridge for obtaining a second reading.

47. The system of claim 42 wherein said second pneumatic pathway comprises a valve unit having a pair of inlet devices fluidly connected thereto, a first inlet device adapted to receive said first gas; a second inlet device adapted to receive said suspect gas and having a conduit with a reservoir of a predetermined volumetric capacity interposed therein, and valve means operable to retain said suspect gas within said reservoir and to release said suspect gas from said reservoir for passage to said valve unit, said valve unit operable to convey either said first gas or said suspect gas toward said sensor means.

* * * * *